(12) United States Patent
Wu et al.

(10) Patent No.: US 6,904,120 B2
(45) Date of Patent: Jun. 7, 2005

(54) METHOD AND APPARATUS FOR CORRECTING BONE INDUCED SPECTRAL ARTIFACTS

(75) Inventors: Xiaoye Wu, Rexford, NY (US); James LeBlanc, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/611,477

(22) Filed: Jul. 1, 2003

(65) Prior Publication Data

US 2005/0002484 A1 Jan. 6, 2005

(51) Int. Cl.⁷ .................................................. A61B 6/00
(52) U.S. Cl. .......................................... 378/19; 378/207
(58) Field of Search ............................ 378/4, 18, 19, 378/207

(56) References Cited

U.S. PATENT DOCUMENTS 4,149,081 A * 4/1979 Seppi ........................... 378/5
5,774,519 A * 6/1998 Lindstrom et al. ............. 378/18
6,115,487 A * 9/2000 Toth et al. .................. 382/131

* cited by examiner

*Primary Examiner*—Craig E. Church
*Assistant Examiner*—Jurie Yun
(74) *Attorney, Agent, or Firm*—Fletcher Yoder

(57) ABSTRACT

The present technique provides for the estimation and correction of bone induced spectral (BIS) artifacts. Spectral matching is employed to approximate the incident X-ray spectrum attenuated by bone and water with an X-ray spectrum attenuated by water alone. A table can be built to express the amount in apparent projection value shift for objects containing bone and water compared with water-like object when their corresponding normalized spectra match. The BIS error may thereby be determined from existing spectral error data obtained from spectral calibration. A corresponding correction factor may be determined from the shift value.

21 Claims, 5 Drawing Sheets

METHOD AND APPARATUS FOR CORRECTING BONE INDUCED SPECTRAL ARTIFACTS

BACKGROUND OF THE INVENTION

The present invention relates generally to the field of medical imaging. In particular, the following techniques relate to computed tomography imaging systems and the calibration of detectors used in such systems.

Computed tomography (CT) imaging systems measure the intensity of X-ray beams passed through a patient from numerous angles. With sufficient angular coverage around the patient, cross-sectional images can be formed, revealing the inner structure of the scanned object. The images are typically displayed on a cathode ray tube, and may be printed or reproduced on film. A virtual 3-D image may also be produced by a CT examination.

CT scanners operate by projecting fan shaped or cone shaped X-ray beams from an X-ray source that is collimated and passes through the object, such as a patient. The attenuated beams are then detected by a set of detector elements. The detector element produces a signal based on the intensity of the X-ray beams. The measured data are then processed to represent the line integrals of the attenuation coefficients of the object along the ray paths. The processed data are typically called projections. By using reconstruction techniques, such as filtered backprojection, cross-sectional images are formulated from the projections. The locations of pathologies may then be identified either automatically, such as by a computer-assisted diagnosis (CAD) algorithm or, more conventionally, by a trained radiologist. CT scanning provides certain advantages over other types of techniques in diagnosing disease particularly because it illustrates the accurate anatomical information about the body. Further, CT scans may help physicians distinguish between types of abnormalities more accurately.

To obtain accurate CT images, a number of calibration and correction algorithms may be applied. One such calibration is spectral calibration. The spectral calibration process generally employs calibration phantoms composed of materials such as water or plastic, which presumably attenuate X-rays passing through the phantom in a manner similar to soft tissue. The respective spectral response of each detector channel is then determined and a correction factor for each detector channel is generated to normalize the respective spectral responses.

In general, the spectral calibration addresses sources of spectral error, i.e., errors arising from changes of the X-ray spectrum. For instance, one example of spectral error may be X-ray beam hardening, also known as "cupping," which manifests as non-uniformities in the imaged water or soft tissue. In particular, because X-ray attenuation coefficients are a function of X-ray photon energy, the polychromatic nature of the X-rays generated by an X-ray tube may lead to spectral errors which are observed as X-ray beam hardening.

Another source of spectral error, however, arises due to the variation in detector efficiency between the detectors comprising the detector array. For example, detector efficiency variations within an array may generate bone-induced spectral (BIS) image artifacts in images of body parts in which there is a mixture of both soft tissue and bone, such as in head images. The BIS artifacts are typically manifested as a ring or band in the reconstructed image. The source of the BIS artifact is complex, and any imperfection of the imaging system, such as in the detector or the anti-scatter collimator, may contribute to the incidence of BIS artifacts. In particular, the BIS artifacts may be observed when there are discrepancies between the observed and the expected spectral response by the detector, such as when the spectral content incident upon the detector elements is changed due to the presence of bone.

Removal of the BIS artifacts may be problematic even the system has undergone a successful spectral calibration because the derived spectral correction factors are generally useful for correcting image artifacts in regions of water or soft tissue, not bone. Indeed, the BIS artifact typically does not appear in images of test-phantoms, which are made of water-like materials. Furthermore, the correction employed to minimize beam hardening artifacts in the presence of bones, such as in head images, merely functions to remove streaking and to sharpen the boundary between bone and soft tissue in the images. The correction, however, does not account for the spectral response discrepancies between detector elements introduced by bone and, therefore, does not correct BIS artifacts.

Indeed, in general, BIS artifacts are neither characterized nor addressed by a specific calibration or correction procedure. Instead, a detector array may be configured to ensure similar spectral response of the detector channels which image at or near the isocenter of the imaging volume. This approach may involve physically swapping detector modules such that higher quality or similarly spectrally responsive modules are positioned in the portion of the detector that samples rays of the isocenter region. In addition to the rather arbitrary nature of this approach, the module swapping process is time consuming and cannot be relied upon to generate consistent results between detectors. Further, with the development volumetric CT, the swapping process is more difficult, simply due to the increased number of channels in the detector module. A fast, reproducible, and reliable technique for correcting BIS artifacts in reconstructed images is therefore desirable.

BRIEF DESCRIPTION OF THE INVENTION

The present technique provides a novel approach for estimating bone induced spectral (BIS) artifacts. In particular, the present technique estimates the BIS artifacts in a spectrally calibrated X-ray detection system using the presumed linearity of the X-ray detection system. The presumed linearity provides that, under the spectrum incident to the detector, the detected signal should be proportional to the X-ray flux. Once a BIS artifact is estimated, a suitable correction may be calculated and applied to generate images substantially free of BIS artifacts.

For example, measured X-ray data may be processed with a set of corrections, including a spectral correction, to form the line-integral of the attenuation coefficient at a given x-ray path. The spectral correction may be based on the apparent projection value, i.e., the logarithmic value of the ratio of the x-ray intensity measured with the object and the x-ray intensity measured without object. The spectral error being corrected, however, is generally a function of the X-ray spectrum incident to the detector, not the apparent projection value. The use of the apparent projection value to derive the spectral correction for imaging objects made purely of water is justified because of the one-to-one relationship between the X-ray spectrum incident to the detector and the apparent projection valve. However, for objects comprising water and bone, such as the human body, multiple spectral shapes can yield the same apparent projection valve, meaning no one-to-one relationship exists between the X-ray spectrum incident to the detector and the apparent projection value for images containing bone. The present technique is generally directed to identifying the spectral shape attenuated by water alone which is closest to the spectral shape attenuated by a given amount of water and bone. The correction for spectral error may then be based upon the apparent projection value associated with the spectral shape attenuated by water alone, which provides a good spectral match. The resulting correction addresses spectral error associated with the presence of bone in the imaged area, including BIS artifacts.

In one embodiment of the present technique, a method for estimating a BIS artifact for a detector element is provided. A first incident X-ray spectrum attenuated by water and a second incident X-ray spectrum attenuated by bone and water are acquired at a detector element. The first incident spectrum may be scaled to produce a scaled spectrum corresponding to the second incident spectrum. The scaled spectrum differs from the first incident spectrum at a projection value by an apparent projection value shift which corresponds to a BIS artifact at the projection value for the detector element.

In another embodiment of the present technique, a CT image analysis system is provided. The system comprises an X-ray source configured to emit a stream of radiation and a detector configured to detect the stream of radiation and to generate one or more signals responsive to the stream of radiation. The detector comprises a plurality of detector elements. The system also includes a system controller configured to control the X-ray source and to acquire projection data for one or more of the detector elements via a data acquisition system. The projection data may comprises a first incident X-ray spectrum attenuated by water and a second incident X-ray spectrum attenuated by bone and water at the one or more detector elements. In addition, the system comprises a computer system. The computer system may be configured to scale the first incident spectrum to produce a scaled spectrum. The scaled spectrum corresponds to the second incident spectrum and differs from the first incident spectrum by an apparent projection value shift corresponding to a BIS artifact for the one or more detector elements.

In a further embodiment of the present technique, a CT image analysis system is provided. The system comprises an X-ray source configured to emit a stream of radiation and a detector configured to detect the stream of radiation and to generate one or more signals responsive to the stream of radiation. The detector comprises a plurality of detector elements. The system also includes a system controller configured to control the X-ray source and to acquire projection data for one or more of the detector elements via a data acquisition system. In addition, the system comprises a computer system configured to receive the projection data and to reconstruct the projection data to form an image and an operator workstation configured to display the image. Means for estimating a BIS artifact using spectral matching is also present.

In an additional embodiment of the present technique, a computer program is provided on one or more computer readable media, for estimating a BIS artifact for one or more detector elements. The computer programs comprises a routine for acquiring a first incident X-ray spectrum attenuated by water for each of one or more detector elements and a routine for acquiring a second incident X-ray spectrum attenuated by bone and water at each of the one or more detector elements. In addition, the computer program includes a routine for scaling the first incident spectrum to produce a scaled spectrum which corresponds to the second incident spectrum. The scaled spectrum differs from the first incident spectrum by an apparent projection value shift which corresponds to a BIS artifact at the projection value for the respective detector element.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
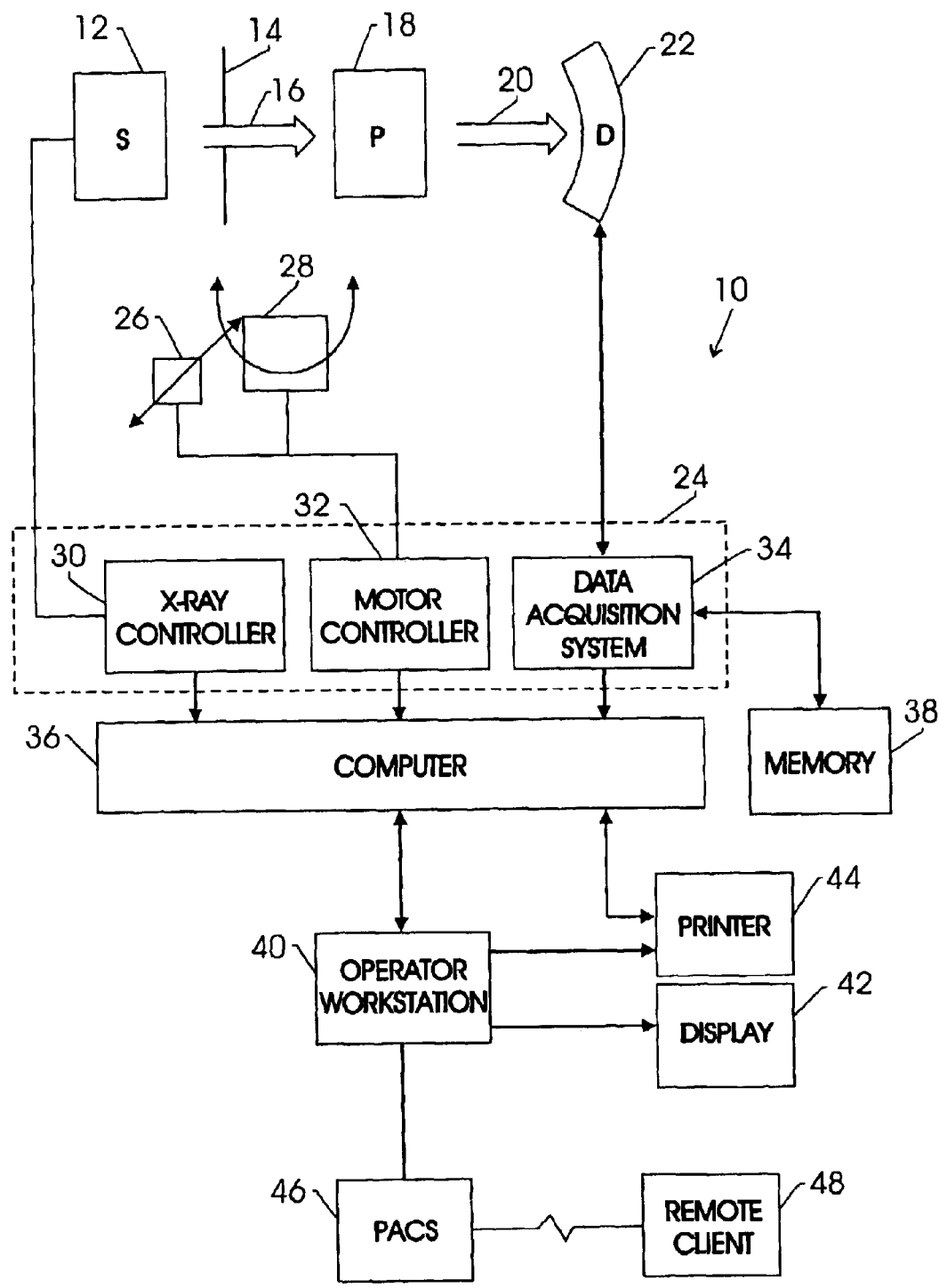
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the illustrated embodiment, system 10 is a computed tomography (CT) system designed both to acquire original image data, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 and moreover, to a memory 38. It should be understood that any type of memory to store a large amount of data might be utilized by such an exemplary system 10. Moreover, the memory 38 may be located at this acquisition system or may include remote components for storing data, processing parameters, and routines described below.

The computer 36 is configured to receive commands and scanning parameters from an operator via an operator workstation 40 typically equipped with a keyboard and other input devices. Various operational and communication routines or modules, such as a computer program implementing the techniques described herein, may be stored locally on the computer 36, remotely on other systems, such as the remote client 48, or on one or more readable media, such as optical or magnetic disks, accessible to the computer 36. The operator may access and execute the stored routines or modules in operating the imaging system 10.

An operator may control the system 10 via the input devices. Thus, the operator may observe the reconstructed image and other data relevant to the system from computer 36, initiate imaging, and so forth. Similarly, a display 42 coupled to the operator workstation 40 may allow an operator to observe the reconstructed image and to control imaging. Additionally, the scanned image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image and to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
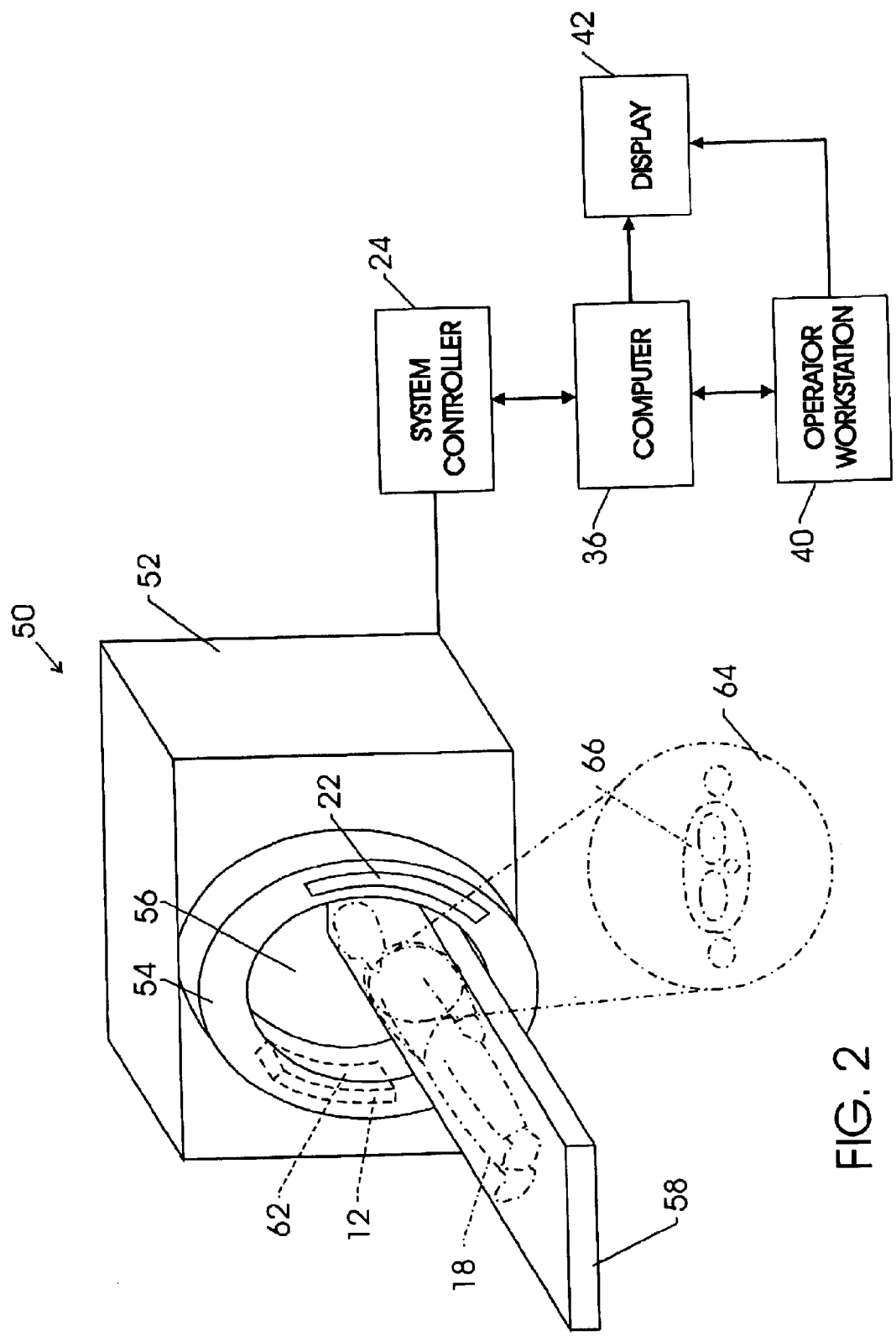
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is typically a multi-slice detector CT (MDCT) system that offers a wide array of axial coverage, high gantry rotational speed, and high spatial resolution, all of which allow the use of sophisticated cardiac reconstruction algorithms. The CT scanning system 50 is illustrated with a frame 52 and a gantry 54 that has an aperture 56. The aperture 56 may typically be 50 cm in diameter. Further, a patient table 58 is illustrated positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 26 (see FIG. 1). The gantry 54 is illustrated with the source of radiation 12, typically an X-ray tube that emits X-ray radiation from a focal point 62. For cardiac imaging, the stream of radiation is directed towards the heart of the patient 18.

In typical operation, X-ray source 12 projects an X-ray beam from the focal point 62 and toward detector array 22. The detector 22 is generally formed by a plurality of detector elements, which sense the X-rays that pass through and around a subject of interest, such as the heart and chest. Each detector element produces an electrical signal that represents the intensity of the X-ray beam at the position of the element at the time the beam strikes the detector. Furthermore, the gantry 54 is rotated around the subject of interest so that a plurality of radiographic views may be collected by the computer 36. Thus, an image or slice is computed which may incorporate, in certain modes, less or more than 360 degrees of projection data, to formulate an image. The image is collimated to desired dimensions, typically less than 40 mm thick using either lead shutters in front of the X-ray source 12 and different detector apertures. The collimator 14 (see FIG. 1) typically defines the size and shape of the X-ray beam that emerges from the X-ray source 12. In addition, a bowtie filter may be included in the system 50 to further control the patient dose. In particular, the bowtie filter pre-attenuates the X-rays to accommodate the body part being imaged, such as head or torso, such that, in general, greater attenuation is provided for X-ray passing through or near the isocenter 72. In this manner, the bowtie filter conforms the X-ray intensity during imaging in accordance with the region being imaged.

Thus, as the X-ray source 12 and the detector 22 rotate, the detector 22 collects data of the attenuated X-ray beams. The data collected by the detector 22 undergoes pre-processing and calibration to condition the data to represent the line integrals of the attenuation coefficients of the scanned objects. The processed data, commonly called projections, are then filtered and backprojected to formulate an image of the scanned area. As mentioned above, the computer 36 is typically used to control the entire CT system 10. The main computer that controls the operation of the system may be adapted to control features enabled by the system controller 24. Further, the operator workstation 40 is coupled to the computer 36 as well as to a display, so that the reconstructed image may be viewed. Alternatively, some or all of the processing described herein may be performed remotely by additional computing resources based upon raw or partially processed image data.

Once reconstructed, the image produced by the system of FIGS. 1 and 2 reveals internal features of a patient. As illustrated generally in FIG. 2, the image 64 may be displayed to show these features, such as indicated at reference numeral 66 in FIG. 2. In traditional approaches to diagnosis of medical conditions, such as disease states, and more generally of medical events, a radiologist or physician would consider a hard copy of display of the image 64 to discern characteristic features of interest. Such features might include lesions, sizes and shapes of particular anatomies or organs, and other features which would be discernable in the image based upon the skill and knowledge of the individual practitioner. Other analyses may be based upon capabilities of various CAD algorithms with subsequent processing and data acquisition at the discretion of the practitioner.

In diagnostic applications, the measured signal is typically attenuated by bone and soft tissue. The signal, p, measured by a detector may generally be represented as:

$$p=-\log{(K\Sigma R(E)S(E)E)}+\log{(K\Sigma R(E)S_a(E)E)} \quad (1)$$

where E is photon energy, R(E) is the detector channel efficiency for E, S(E) is the X-ray spectrum incident to the detector channel through an object, $S_a(E)$ is the X-ray spectrum through air, Σ represents a summation over E, and K is a constant if the gain of the detector channel is linear. While S(E) is dependent on the material being imaged, generally soft tissue and bone, $S_a(E)$ is independent of the material being imaged. The differential spectral error, Δ, of a detector channel can be expressed as:

$$\Delta=-\log{[(\Sigma R_1(E)S(E)E)/(\Sigma R_0(E)S(E)E)]}+\log{[(\Sigma R_1(E)S_a(E)E)/(\Sigma R_0(E)S_a(E)E)]} \quad (2)$$

where $R_1$ is the detection efficiency of a detector channel for E, and $R_0$ is the common mode detector efficiency for E. The differential spectral error associated with a detector, therefore, is a function of the X-ray spectrum incident on the channel weighted by detector response.

Because of the attenuating effects of bone, noted above, a reconstructed diagnostic image may include BIS artifacts that present themselves as a ring or band centered about the isocenter of the imaged volume and may, therefore, obscure or distract from a diagnostic region of interest. In general, the BIS artifacts occur due to the change in spectral content incident on the detector elements caused by the presence of bone in the imaging volume. In addition, imaging system imperfections, particularly those associated with the detector and the collimator, may affect the incidence and severity of the BIS artifacts. The BIS artifacts are generally not addressed by the spectral calibration process, which does not account for the effects of bone or bone-like material in the X-ray path.

More precisely, BIS artifacts may result when the −log of a projection value obtained during calibration is used for spectral correction during diagnostic imaging. In particular, due to the nature of the detection process, the appropriate differential spectral error should be a function of incident spectral shape, S(E), as indicated in equation (2), which can be simplified as, $$\Delta=f(S(E)) \quad (3)$$

where S(E) is the normalized X-ray spectrum incident to a channel. In practice, spectral correction may instead be based on:

$$\Delta=F(p) \quad (4)$$

where the analytical or numerical function F( ) is the spectral error correction function, obtained from the spectral calibration process, and p is the projection value. In general, the spectral correction function obtained from spectral calibration contains both the beam-hardening and detector response errors. Since the BIS artifacts are associated only with differential detector response errors, the function F(p) indicates only detector response errors.

Figure 3:
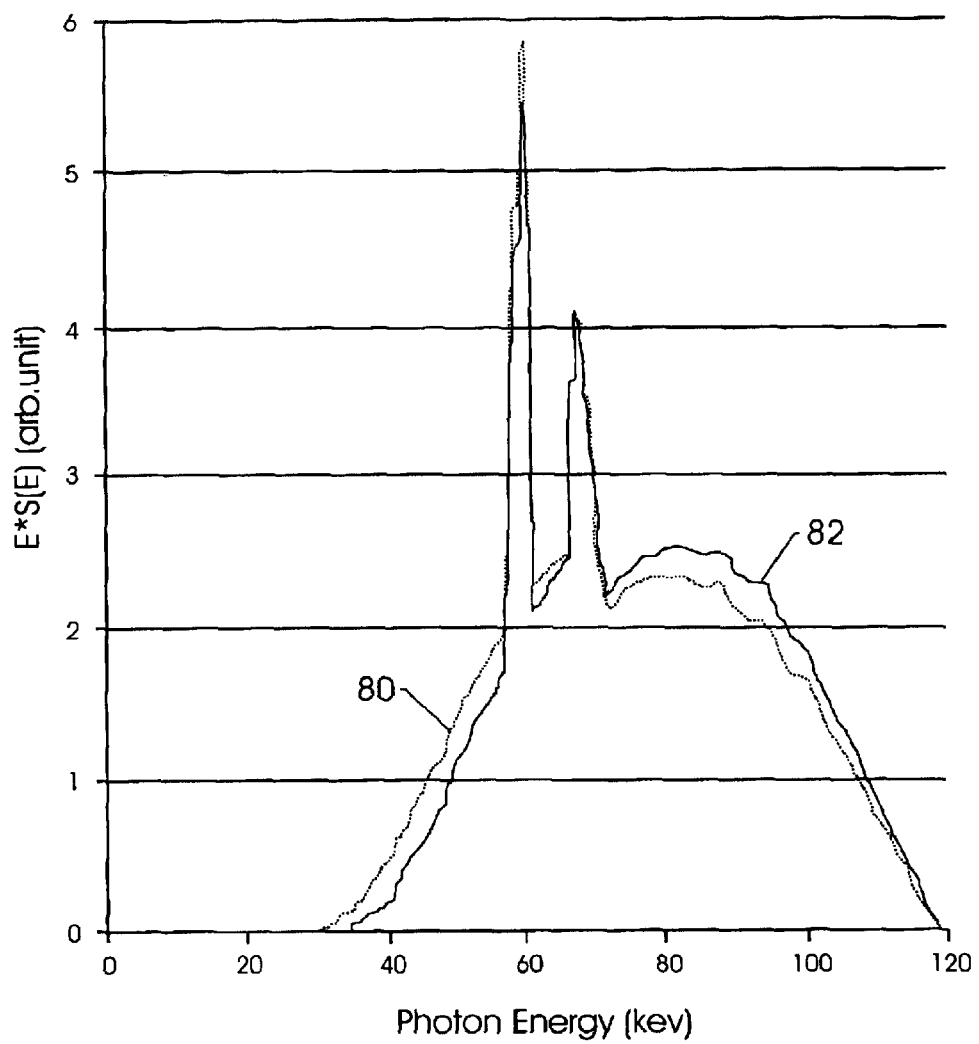
FIG. 3 is a chart of incident X-ray spectra attenuated by water and bone and by water alone, which yield the same apparent projection value.

However, as depicted in FIG. 3, a projection value, represented along the horizontal axis as photon energy, can be associated with more than one, X-ray incident spectra, S(E). In particular, in FIG. 3, the X-ray spectra error for water 80 and for water plus bone 82 are depicted, illustrating the non-equivalence of the two spectra. The absence of a unique X-ray spectrum for a given projection value in conjunction with the use of projection values as a surrogate measure of S(E) can, thereby, generate BIS artifacts in the reconstructed image.

In general, the projection values can be decomposed into two parts $$p_t => p_w + p_b \quad (5)$$

where $p_t$ is the total projection value, $p_w$ and $p_b$ are contributed by water and bone component, respectively. The suitable spectral correction should therefore be:

$$F(p_t + g(p_t, p_b)) \quad (6)$$

in order to maintain the same incident spectrum upon a detector channel as the spectrum calibrated during the spectral calibration, where $g(p_t, p_b)$ is the extra projection value needed to make the normalized incident spectrum attenuated by bone and water match the one attenuated by water-only.

As stated above, the differential error is not a function of projection value p, instead, it is a function of normalized incident spectrum S(E) or, equivalently, a function of ($p_t$, $p_b$). In the absence of bones, projection value p and spectrum S(E) have one-to-one relationship. This relationship, however, is not maintained when there is bone in the projection path. The difference is the BIS correction value for a given detector channel, which can be expressed as:

$$B(p_t, p_b) = F(p_t + g(p_t, p_b)) - F(p_t). \quad (7)$$

The function $g(p_t, p_b)$, may be obtained by the process of spectral matching and may thereby be determined based upon the initial X-ray spectrum independent of the properties of the detector 22 or the constituent detector elements. In one embodiment, the term $p_b$ may be obtained during bone processing of the image, such as during an iterative bone option (IBO). The term $B(p_t, p_b)$ may be determined and added to the backprojection step associated with bone processing to correct for BIS artifacts.

Figure 4:
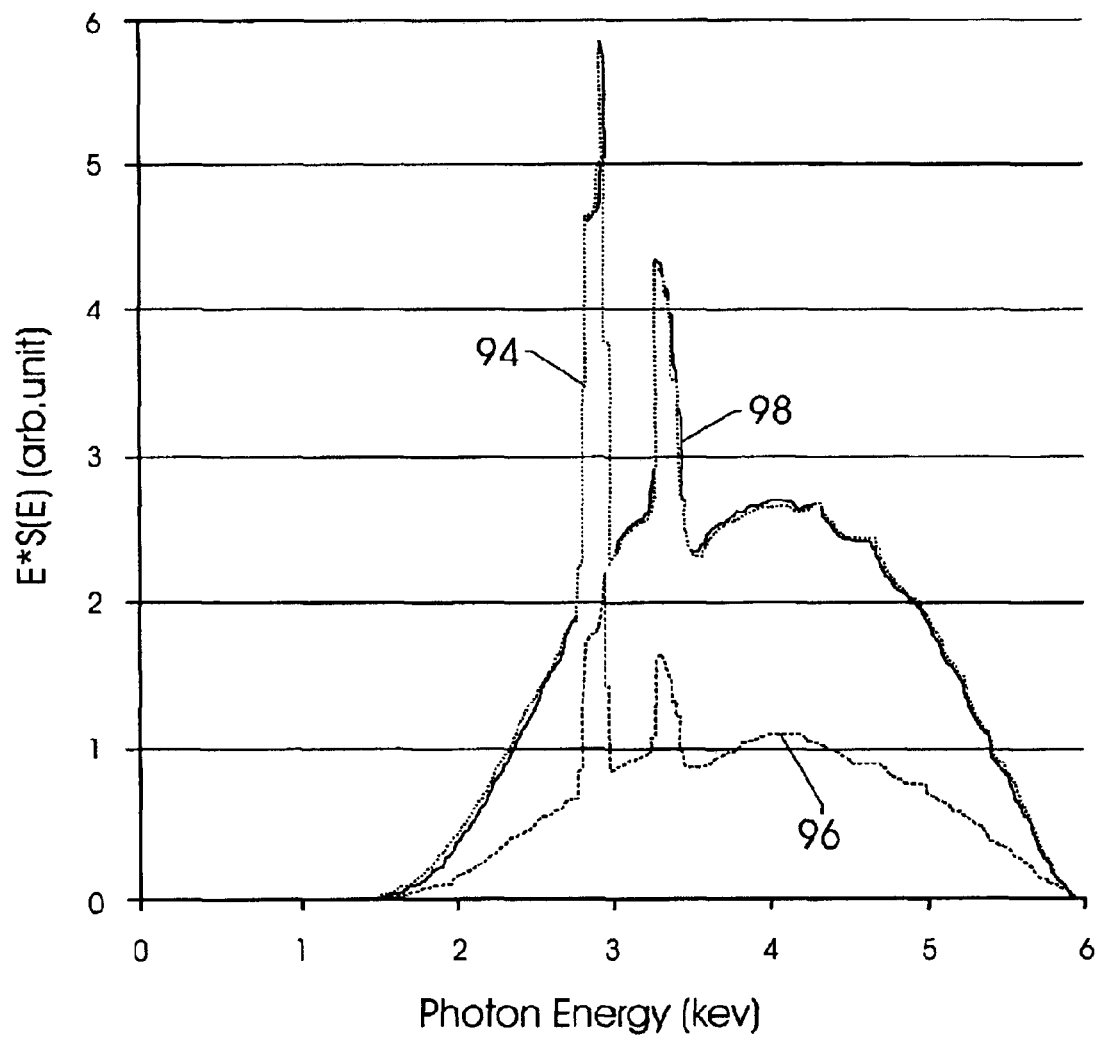
FIG. 4 is a chart depicting unscaled X-ray spectra attenuated by water and bone and by water, along with a scaled X-ray spectra attenuated by water.

The spectral matching process is based upon matching the incident X-ray spectrum attenuated by bone and water to the spectrum attenuated by water only, i.e., the calibration spectrum. The spectra to be matched normally differ by a scaling factor, which does not play a role in differential errors, since the constant cancels out, as seen in equation (2), as long as the detection system response is linear for a given incident X-ray spectrum. For example, referring to FIG. 4, an X-ray spectrum attenuated by bone and water, i.e., bone and water spectrum 94, is depicted. The bone and water spectrum 94 depicted results from an embodiment in which 120 kVp are applied to the tube at the source 12 to generate X-rays 16, which are attenuated by 10 cm of water and 1.5 cm of bone, yielding a p value of 2.698. In this embodiment, a corresponding, i.e., similarly shaped, water spectrum 96 is generated using 18.7 cm of water to attenuate the X-rays 16, yielding a respective p value of 3.678. Though the water spectrum 96 substantially corresponds to the bone and water spectrum 94 in shape, the two spectra are offset from one another. However, the water spectrum 96 may be scaled, such as by the factor 2.64 depicted in FIG. 4, to form a shifted spectrum 98 which approximates the bone and water spectrum 94. An apparent projection value shift, 0.98 in this case (i.e., 3.678–2.698), corresponds to a point in the function $g(p_t, p_b)$ or, equivalently, $g(p_w, p_b)$. In this manner a corrected projection value for the water attenuated spectrum 96, i.e., the shifted spectrum 96, may be derived which corresponds to the bone and water spectrum 94 for the range of desired bone and water path lengths. An appropriate BIS correction factor may then be determined based upon the determined apparent projection value shift obtained in matching the water spectrum 96 and the bone and water spectrum 94.

Figure 5:
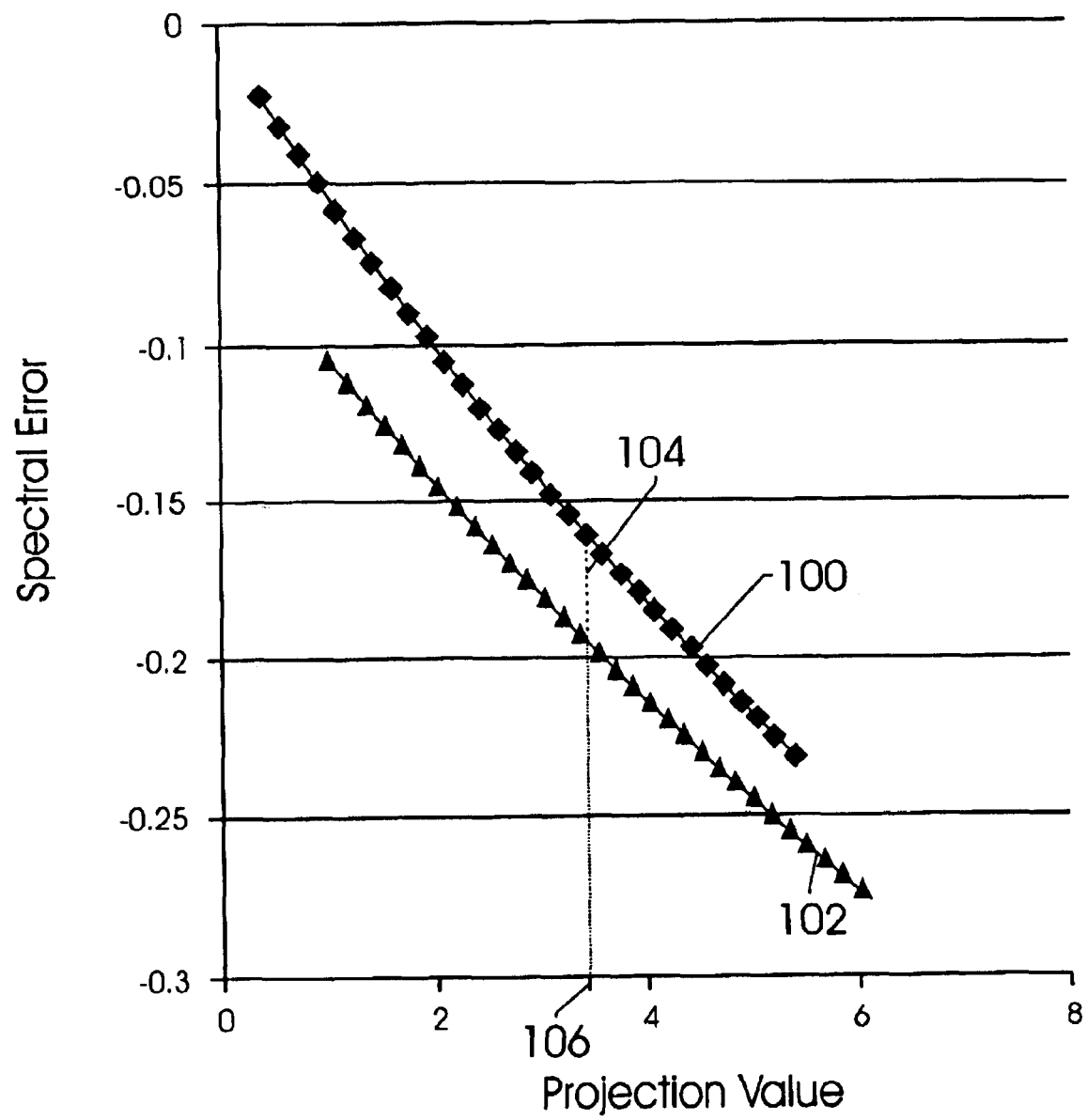
FIG. 5 is a chart depicting spectral error attenuated by water and bone and by water along with a spectral error extracted through spectral matching based on spectral calibration data.

By repeating the matching process for each detector element of interest, a matrix or table of the projection shift functions, $g(p_t, p_b)$, for each element may be obtained, such as by resampling $p_t$ and $p_b$ at equal intervals or by deriving a functional form for $g(p_t, p_b)$. The projection shift function may then be used for rapid corrections during the imaging process. For instance, in one embodiment, a software routine may be utilized which models the initial incident spectrum at a given channel for the possible thickness of water and bone which might be observed in a typical patient scan. An example of such an initial incident spectrum model is depicted in FIG. 5. The water spectral error 100, as determined from the spectral calibration, is plotted as a function of projection value. Similarly, the projected spectral error 102 associated with 1.5 cm of bone and a varying amount of water is plotted. The bone spectral error 102 may be derived from based on the given detector elements spectral response, such as via spectral matching based on the water spectral error 100. The difference 104 between the water spectral error 100 and the bone spectral error 102 at a given projection value 106 constitutes the BIS artifact associated with a reconstructed image at that projection value 106. A suitable BIS correction factor for the detector element may be determined from this difference. If a bowtie filter is employed in the imaging system, such as to control the patient dose of X-rays, the matching process may be performed for the detector elements with corresponding initial X-ray spectra.

The BIS correction factor, $F(p_t+g(p_t, p_b))-F(p_t)$, may be applied by itself or may be combined with other correction factors as part of a more general correction process. For example, the BIS correction factor can be added to an iterative bone correction factor which may be a function of $p_b, p_t,$ and $p_b,$ or $p_w$ and $p_b$. The combined correction factors may then be used in image reconstruction, such as to reduce or eliminate beam hardening and BIS artifacts. The resulting images may be displayed for evaluation or diagnosis by medical personnel.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for estimating a BIS artifact for a detector element, the method comprising:
   acquiring a first incident X-ray spectrum attenuated by water and a second incident X-ray spectrum attenuated by bone and water at a detector element; and
   scaling the first incident spectrum to produce a scaled spectrum which corresponds to the second incident spectrum, wherein the scaled spectrum differs from the first incident spectrum at a projection value by an apparent projection value shift which corresponds to a BIS artifact at the projection value for the detector element.

2. The method as recited in claim 1, further comprising:
   generating a BIS correction factor based upon the BIS artifact at the projection value; and
   reconstructing an image using the BIS correction factor.

3. The method as recited in claim 2, further comprising:
   combining the BIS correction factor with one or more other correction factors.

4. The method as recited in claim 2, further comprising displaying the image.

5. The method as recited in claim 1, wherein the first incident X-ray spectrum is a calibration spectrum.

6. The method as recited in claim 1, wherein the first incident X-ray spectrum reflects the X-ray attenuation through varying path lengths of water.

7. The method as recited in claim 1, wherein the second incident X-ray spectrum reflects the X-ray attenuation through varying path lengths of bone and water.

8. The method as recited in claim 1, further comprising:
   determining the BIS artifact for each of one or more additional detector elements; and
   generating a matrix of BIS correction factors associated with the respective detector elements.

9. The method as recited in claim 8, further comprising reconstructing an image using the matrix of BIS correction factors.

10. The method as recited in claim 9, further comprising displaying the image.

11. A CT image analysis system comprising:
    an X-ray source configured to emit a stream of radiation;
    a detector configured to detect the stream of radiation and to generate one or more signals responsive to the stream of radiation, wherein the detector comprises a plurality of detector elements;
    a system controller configured to control the X-ray source and to acquire projection data from one or more of the detector elements via a data acquisition system, wherein the projection data comprises a first incident X-ray spectrum attenuated by water and a second incident X-ray spectrum attenuated by bone and water at the one or more detector elements; and
    a computer system configured to scale the first incident spectrum to produce a scaled spectrum which corresponds to the second incident spectrum and differs from the first incident spectrum by an apparent projection value shift corresponding to a BIS artifact for the one or more detector elements.

12. The CT image analysis system as recited in claim 11, wherein the computer system is further configured to generate a BIS correction factor for each detector element based upon the BIS artifact and to reconstruct an image using the BIS correction factors.

13. The CT image analysis system as recited in claim 12, further comprising an operator workstation configured to display the reconstructed image.

14. A CT image analysis system comprising:
  means for acquiring a first incident X-ray spectrum attenuated by water and a second incident X-ray spectrum attenuated by bone and water at a detector element of a detector ; and
  means for scaling the first incident spectrum to produce a scaled spectrum which corresponds to the second incident spectrum, wherein the scaled spectrum differs from the first incident spectrum at a projection value by an apparent projection value shift which corresponds to a BIS artifact at the projection value for the detector element.

15. The CT image analysis system as recited in claim 14, further comprising:
  means for generating a BIS correction factor based upon the BIS artifact at the projection value; and
  means for reconstructing an image using the BIS correction factor.

16. A computer-readable medium, comprising:
  a routine for acquiring a first incident X-ray spectrum attenuated by water for each of one or more detector elements;
  a routine for acquiring a second incident X-ray spectrum attenuated by bone and water at each of the one or more detector elements; and
  a routine for scaling the first incident spectrum to produce a scaled spectrum which corresponds to the second incident spectrum, wherein the scaled spectrum differs from the first incident spectrum by an apparent projection value shift which corresponds to a BIS artifact at the projection value for the respective detector element.

17. The computer-readable medium as recited in claim 16, further comprising:
  a routine for generating a BIS correction factor for each detector elements based upon the BIS artifact at the projection value; and
  a routine for reconstructing an image using the BIS correction factors.

18. The computer-readable medium as recited in claim 17, further comprising a routine for combining the BIS correction factors with one or more other correction factors for each detector element.

19. The computer-readable medium as recited in claim 17, further comprising a routine for displaying the image.

20. The computer-readable medium as recited in claim 16, wherein the first incident X-ray spectrum is a calibration spectrum.

21. The computer-readable medium as recited in claim 16, wherein the second incident X-ray spectrum reflects the X-ray attenuation through varying path lengths of bone and water.

* * * * *